United States Patent
Nishimura et al.

(10) Patent No.: US 11,274,089 B2
(45) Date of Patent: Mar. 15, 2022

(54) 5-HYDROXYMETHYL-2-FURFURAL PRODUCTION METHOD

(71) Applicant: NIHON SHOKUHIN KAKO CO., LTD., Tokyo (JP)

(72) Inventors: Yuichi Nishimura, Shizuoka (JP); Norihisa Hamaguchi, Shizuoka (JP); Hitoshi Takaguchi, Shizuoka (JP)

(73) Assignee: NIHON SHOKUHIN KAKO CO., LTD., Tokyo (JP)

( * ) Notice: Subject to any disclaimer, the term of this patent is extended or adjusted under 35 U.S.C. 154(b) by 151 days.

(21) Appl. No.: 16/312,566

(22) PCT Filed: May 9, 2017

(86) PCT No.: PCT/JP2017/017552
§ 371 (c)(1),
(2) Date: Dec. 21, 2018

(87) PCT Pub. No.: WO2018/003295
PCT Pub. Date: Jan. 4, 2018

(65) Prior Publication Data
US 2019/0330172 A1    Oct. 31, 2019

(30) Foreign Application Priority Data

Jun. 27, 2016 (JP) .............................. JP2016-126272
Apr. 19, 2017 (JP) .............................. JP2017-082634

(51) Int. Cl.
  *C07D 307/48* (2006.01)
  *A23L 33/10* (2016.01)
  *B01J 21/18* (2006.01)
  *C07D 307/46* (2006.01)
  *C08G 63/16* (2006.01)

(52) U.S. Cl.
  CPC .............. *C07D 307/48* (2013.01); *A23L 33/10* (2016.08); *B01J 21/18* (2013.01); *C07D 307/46* (2013.01); *C08G 63/16* (2013.01); *A23V 2002/00* (2013.01)

(58) Field of Classification Search
  CPC ...... C07D 307/48; C07D 307/46; A23L 33/10
  See application file for complete search history.

(56) References Cited

U.S. PATENT DOCUMENTS

| | | | |
|---|---|---|---|
| 2014/0371473 A1 | 12/2014 | Blank et al. | |
| 2015/0031904 A1 | 1/2015 | Cho et al. | |
| 2015/0141584 A1 | 5/2015 | Saywell et al. | |
| 2017/0197930 A1* | 7/2017 | Sokolovskii | C07D 307/68 |

FOREIGN PATENT DOCUMENTS

| | | | | |
|---|---|---|---|---|
| CN | 103127296 | * | 6/2013 | ........... A61K 31/804 |
| EP | 0561928 | | 2/1996 | |
| JP | H06-504272 | | 5/1994 | |
| JP | 2010-265468 | | 10/1998 | |
| JP | H10265468 | | 10/1998 | |
| JP | 2008088134 | | 4/2008 | |
| JP | 2008193933 | | 8/2008 | |
| JP | 2008-207995 | | 9/2008 | |
| JP | 2009-1519 | | 1/2009 | |
| JP | 2010-168238 | | 8/2010 | |
| JP | 2011136959 | | 7/2011 | |
| JP | 2011176043 | | 9/2011 | |
| JP | 2013-203665 | | 10/2013 | |
| JP | 2015-506389 | | 3/2015 | |
| JP | 2015-513356 | | 5/2015 | |
| WO | 2010077133 | | 7/2010 | |
| WO | 2013146085 | | 10/2013 | |
| WO | 2014180979 | | 11/2014 | |

OTHER PUBLICATIONS

CN 103127296; Machine English traslation; 2013.*
International Search Report and Written Opinion in corresponding PCT/JP2017/017552, dated Aug. 8, 2017 (English translation attached).
Kilic, et al., "Fructose Dehydration to 5-Hydroxymethylfurfural over Sulfated TiO2-SiO2, Ti-SBA-15, ZrO2, SiO2, and Activated Carbon Catalysts", Ind. Eng. Chem. Res. 2015, 54, 19, 5220-5225.
Wang, et al., "Efficient catalytic conversion of fructose into hydroxymethylfurfural by a novel carbon-based solid acid", Green Chemistry, 2011, vol. 13, issue 10, pp. 2678-2681.
Yang, et al., "Dehydration of Fructose into 5-Hydroxymethylfurfural Catalyzed by Phosphorylated Activated Carbon Catalyst", Asian Journal of Chemistry, 2015, vol. 27, issue 8, pp. 2979-2982.
Qi, et al., "Acid-catalyzed dehydration of fructose into 5-hydroxymethylfurfural by cellulose-derived amorphous carbon", ChemSusChem., Nov. 2012, vol. 5, issue 11, pp. 2215-2220.
Liu, et al., "Conversion of fructose into 5-hydroxymethylfurfural and alkyl levulinates catalyzed by sulfonic acid-functionalized carbon materials", Green Chemistry, 2013, vol. 15, issue 10, pp. 2895-2903.
Russo, et al., "Solid acids with SO3H groups and tunable surface properties: versatile catalysts for biomass conversion", Journal of Materials Chemistry A, 2014, vol. 2, issue 30, pp. 11813-11824.
Fabicovicova, et al., "Hydrogenolysis of cellulose to valuable chemicals over activated carbon supported mono- and bimetallic nickel/tungsten catalysts", Green Chemistry, 2014, vol. 16, issue 7, pp. 3580-3588.

(Continued)

*Primary Examiner* — Pancham Bakshi
(74) *Attorney, Agent, or Firm* — Hovey Williams LLP

(57) ABSTRACT

An object of the present invention is to provide a method for producing 5-hydroxymethyl-2-furfural (5-HMF) suitable for industrial-scale production and a novel catalyst composition for use in synthesizing 5-HMF. The present invention provides a method for producing 5-HMF comprising performing a dehydration reaction of a carbohydrate comprising a hexose as a constituent sugar or a derivative thereof by using activated carbon as a catalyst; and a catalyst composition for use in the reaction for producing 5-HMF from a carbohydrate comprising a hexose as a constituent sugar through a dehydration reaction, the catalyst composition comprising activated carbon.

14 Claims, 2 Drawing Sheets

(56) References Cited

OTHER PUBLICATIONS

The Chemical Society of Japan, Kagaku Benran Oyo Kagaku-hen, 6th edition, 2003, p. 664 paragraph e., p. 722 paragraph d.
Sairanen, et al., "Functionalized Activated Carbon Catalysts in Xylose Dehydration", Topics in Catalysis, Jun. 2013, vol. 56, issue 9-10, pp. 512-521.
Office Action in corresponding Japanese Patent Application Serial No. 2017-082634, dated Aug. 1, 2017 (English translation attached).
Office Action in corresponding Japanese Patent Application Serial No. 2017-082634, dated Oct. 17, 2017 (English translation attached).
Extended European Search Report in corresponding EP 17819662. 2, dated Jan. 23, 2020.
Mazzotta, et al., "Efficient Solid Acid Catalyst Containing Lewis and Bronsted Acid Sites for the Production of Furfurals", ChemSusChem, 2014, vol. 7, pp. 2342-2350.
Leblanc, et al., "Formation of Hydroxymethylfurfural in Domestic High-Fructose Corn Syrup and Its Toxicity to the Honey Bee (*Apis mellifera*)", J. Agric. Food Chem., 2009, vol. 57, pp. 7369-7376.
Kim, et al., "Facile Production of 5-Hydroxymethyl-2-Furfural from Industrially Supplied Fructose Syrup Using a Wood Powder-Derived Carbon Catalyst in an Ethylene Glycol-Based Solvent", Ind. Eng. Chem. Res., 2014, vol. 53, pp. 4633-4641.

\* cited by examiner

5-HYDROXYMETHYL-2-FURFURAL PRODUCTION METHOD

CROSS-REFERENCE TO RELATED APPLICATIONS

The present application is the U.S. National Stage of International Patent Application No. PCT/JP2017/017552, filed May 9, 2017, which enjoys the benefit of priority from the prior Japanese Patent Application No. 2016-126272 filed on Jun. 27, 2016 and Japanese Patent Application No. 2017-82634 filed on Apr. 19, 2017, the entire disclosures of which are incorporated herein by reference.

TECHNICAL FIELD

The present invention relates to a method for producing 5-hydroxymethyl-2-furfural.

BACKGROUND ART

To establish a sustainable circulating society, the utilization of biomass which is a renewable organism-derived resource is attracting attention. Plastics prepared from biomass are referred to as bioplastics. In recent years, 100% bio-based polyethylene furanoate (PEF) is expected as a novel bioplastic. PEF is a condensation polymer of 2,5-furandicarboxylic acid and ethylene glycol. Produced is 2,5-furandicarboxylic acid (hereinafter abbreviated as "FDCA" in some cases) via 5-hydroxymethyl-2-furfural (5-hydroxymethyl-2-furaldehyde, hereinafter abbreviated as "5-HMF" in some cases) which is a product obtained by dehydration of a carbohydrate.

It is known that 5-HMF can be produced through an intramolecular dehydration reaction using, for example, fructose having a hexose skeleton as a raw material by an acid catalyst. As the acid catalyst for this reaction, homogeneous catalysts such as hydrochloric acid, sulfuric acid and phosphoric acid and heterogeneous catalysts such as strongly acidic cation exchange resins, metal oxides, and immobilized sulfuric acid catalysts are used (Patent Documents 1 and 2). However, the production of 5-HMF using a homogeneous acid catalyst disadvantageously involves the problems of device corrosion by the acid catalyst and difficulty in removal of the acid catalyst from the product, in addition to the problem of many byproducts. A technique of regenerating and using a heterogeneous solid acid catalyst is known in the production of 5-HMF (Patent Document 3). The heterogeneous acid catalyst, however, involves the problems of expensiveness and difficulty in obtainment on an industrial scale, when 5-HMF is produced on an industrial scale.

REFERENCE LIST

Patent Documents

Patent Document 1: JP 2013-203665 A
Patent Document 2: JP H6-504272 T
Patent Document 3: JP 2015-513356 T

SUMMARY OF THE INVENTION

An object of the present invention is to provide a method for producing 5-HMF, which can be carried out inexpensively and simply. Another object of the present invention is to provide a novel catalyst composition for use in synthesizing 5-HMF.

The present inventors have found that a carbohydrate composition comprising 5-HMF can be produced by subjecting, to heating reaction treatment, a carbohydrate composition comprising fructose in the presence of activated carbon, and also found that the activated carbon functions as a catalyst for a dehydration reaction from fructose to 5-HMF. The present inventors have also found that a carbohydrate composition comprising 5-HMF can be produced by subjecting, to heating reaction treatment, a carbohydrate, other than fructose, comprising a hexose as a constituent sugar in the presence of activated carbon. Further, the present inventors have found that the dehydration reaction reduces the production of byproducts in the production of 5-HMF and ensures continuous use of producing facilities, and that the reaction product has a low degree of coloration. The present invention is based on these findings.

The present invention provides the following inventions.

[1] A method for producing 5-hydroxymethyl-2-furfural, comprising performing a dehydration reaction of a carbohydrate comprising a hexose as a constituent sugar or a derivative thereof by using activated carbon as a catalyst.

[2] A method for producing a carbohydrate composition comprising 5-hydroxymethyl-2-furfural by heating a carbohydrate composition comprising one or more selected from the group consisting of carbohydrates comprising a hexose as a constituent sugar and derivatives thereof in the presence of activated carbon at a temperature of 100° C. to 400° C.

[3-1] A method for producing 2,5-furandicarboxylic acid or an ester thereof, comprising subjecting, to an oxidation reaction, the 5-hydroxymethyl-2-furfural obtained by carrying out the method according to [1] or [2].

[3-2] A method for producing 2,5-furandicarboxylic acid or an ester thereof, comprising carrying out the method according to [1] or [2] to produce 5-hydroxymethyl-2-furfural, and subjecting the obtained 5-hydroxymethyl-2-furfural to an oxidation reaction.

[4-1] A method for producing a copolymer, comprising copolymerizing the 2,5-furandicarboxylic acid or ester thereof obtained by carrying out the method according to [3-1] or [3-2] with a different copolymerizable monomer.

[4-2] A method for producing a copolymer, comprising carrying out the method according to [3-1] or [3-2] to produce 2,5-furandicarboxylic acid or an ester thereof, and copolymerizing the obtained 2,5-furandicarboxylic acid or ester thereof with a different copolymerizable monomer.

[5] The method according to [4-1] or [4-2], wherein the different copolymerizable monomer is ethylene glycol and the produced copolymer is polyethylene furanoate.

[6-1] A method for producing a pharmaceutical or food product, comprising blending the 5-hydroxymethyl-2-furfural or derivative thereof obtained by carrying out the method according to [1] or [2].

[6-2] A method for producing a pharmaceutical or food product, comprising carrying out the method according to [1] or [2] to produce 5-hydroxymethyl-2-furfural, optionally derivatizing the obtained 5-hydroxymethyl-2-furfural, and blending the obtained 5-hydroxymethyl-2-furfural or derivative thereof.

[7] A catalyst composition for use in the reaction for producing 5-hydroxymethyl-2-furfural from a carbohydrate comprising a hexose as a constituent sugar or a derivative thereof through a dehydration reaction, the catalyst composition comprising activated carbon.

[8] Use of activated carbon and a composition comprising the activated carbon, as a catalyst for a reaction for producing 5-hydroxymethyl-2-furfural from a carbohydrate comprising a hexose as a constituent sugar or a derivative thereof through a dehydration reaction.

[9] Use of activated carbon and a composition comprising the activated carbon, for the production of a catalyst for a reaction for producing 5-hydroxymethyl-2-furfural from a carbohydrate comprising a hexose as a constituent sugar or a derivative thereof through a dehydration reaction.

The present invention provides a method for producing 5-HMF using activated carbon as a catalyst for a synthesis reaction. Activated carbon is a relatively inexpensive material and can be readily removed outside the system by solid-liquid separation, and thus is advantageous in that 5-HMF can be simply and inexpensively produced on an industrial scale according to the production method of the present invention. The 2,5-furandicarboxylic acid produced from 5-HMF serves as a substitute for terephthalic acid as a raw material for polyethylene terephthalate and is used as a raw material for polyethylene furanoate. Thus, the present invention can be said to be very advantageous in that the invention enables substitution of a petrochemical product PET resin by a resin comprising, as a raw material, biomass which is a renewable resource.

DETAILED DESCRIPTION OF THE INVENTION

Figure 1:
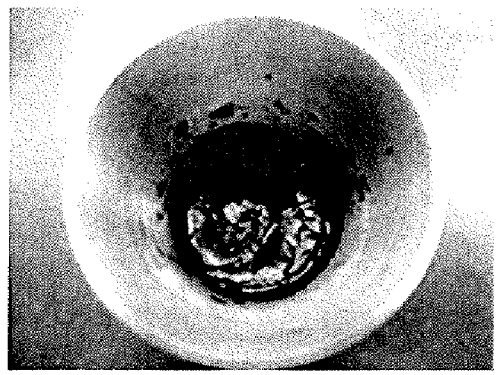
FIG. 1 is a photograph showing a state of a reaction vessel washed with water three times after a reaction using phosphoric acid as a catalyst.
Figure 2:
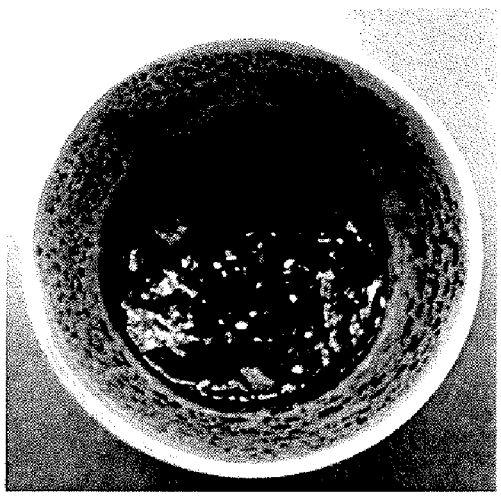
FIG. 2 is a photograph showing a state of a reaction vessel washed with water three times after a reaction using hydrochloric acid as a catalyst.
Figure 3:
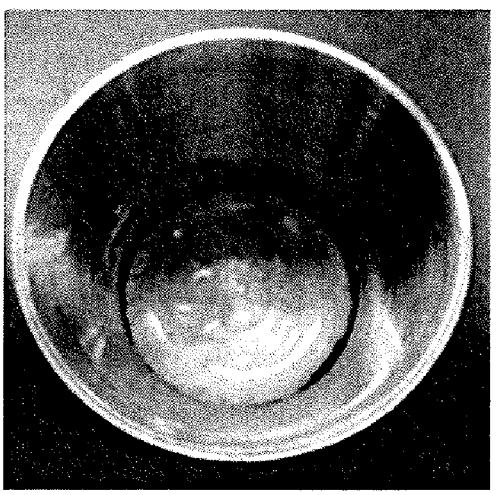
FIG. 3 is a photograph showing a state of a reaction vessel washed with water three times after a reaction using titanium oxide as a catalyst.
Figure 4:
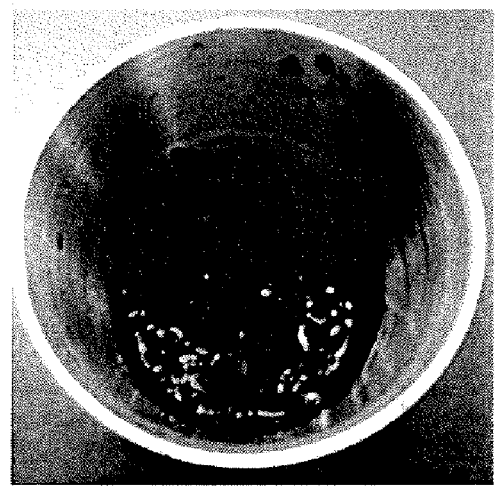
FIG. 4 is a photograph showing a state of a reaction vessel washed with water three times after a reaction using an ion exchange resin as a catalyst.
Figure 5:
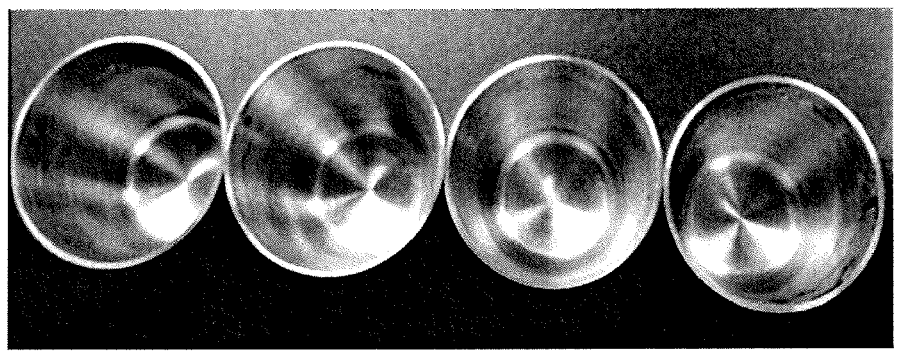
FIG. 5 is a photograph showing a state of reaction vessels washed with water three times after a reaction using activated carbons (activated carbon 1, activated carbon 2, activated carbon 3 and activated carbon 4 from the right side) as catalysts.

The method for producing 5-HMF according to the present invention is characterized by using activated carbon as a catalyst for an intramolecular dehydration reaction from a carbohydrate comprising a hexose as a constituent sugar into 5-HMF.

As the "activated carbon" used in the present invention, a product known as a porous carbonaceous adsorbent can be employed. Activated carbon can mainly be obtained by carbonizing, through heat treatment, a natural carbonaceous material derived from an animal/plant or a mineral, such as coal, coke, pitch, bone charcoal, wood charcoal, coconut shell, wood, sawdust, lignin or bovine bone; an organic polymer such as a synthetic resin, e.g., a phenol resin or polyacrylonitrile; and a carbonaceous material such as soot, and activating the carbonized material.

The "activated carbon" used in the present invention may be either activated carbon itself or a material partially containing activated carbon. Examples of the material partially containing activated carbon include those having activated carbon attached onto a carrier such as a plastic, a mineral, a ceramic or a fiber; those prepared by granulating powdered activated carbon with a pressure-sensitive adhesive; and those granulated from powdered activated carbon and a powder of a mineral, a ceramic or the like. Bone charcoal, wood charcoal, graphite, carbon black and the like may be used as the materials partially containing activated carbon in their structure in the present invention.

The "activated carbon" used in the present invention may be modified activated carbon. For example, it is also possible to use activated carbon in which carboxyl groups are introduced by oxidation reaction treatment with hydrogen peroxide or nitric acid or through air oxidation, and activated carbon in which sulfone groups are introduced by sulfonation treatment with sulfuric acid or fuming sulfuric acid. However, the activated carbon itself has sufficient catalytic activity as is evident from the Examples which will be described later, and thus unmodified activated carbon is preferred as the activated carbon used in the present invention in consideration of its economy, easiness of acquisition and the like.

The "activated carbon" used in the present invention may have a metal carried thereon. That is, the activated carbon subjected to carrying treatment in the present invention refers to activated carbon which, itself, serves as a carrier and has a metal useful as a catalyst on its surface. The metal to be carried on the activated carbon is not particularly limited, and examples thereof include Nb, Ti, Ni and Pd. However, the activated carbon itself has sufficient catalytic activity as is evident from the Examples which will be described later, and thus the activated carbon used in the present invention is preferably activated carbon which is not subjected to carrying treatment in consideration of its economy, easiness of acquisition and the like.

The shape of the activated carbon used in the present invention is not particularly limited, and examples thereof include granular, powdery, fibrous, sheet-like, and honeycomb-like shapes. Specific examples of the activated carbon used in the present invention include powdered carbons such as steam activated carbon, zinc chloride activated carbon and phosphoric acid activated carbon; and granular carbons such as crushed carbon, granulated carbon, granulated carbon and spherical carbon.

When using the powdered activated carbon as the activated carbon used in the present invention, for example, it is possible to use "Shirasagi A, Shirasagi C, and Purified Shirasagi" manufactured by Japan Enviro Chemicals, Ltd.; "Taiko A, Taiko S, and Taiko Y" manufactured by FUTAMURA CHEMICAL CO., LTD; and "CA, CAP, and CASP" manufactured by Norit Japan Co., Ltd. When using the granular activated carbon, for example, it is possible to use "Granular Shirasagi WH and Granular Shirasagi C" manufactured by Japan Enviro Chemicals. Ltd.; "F400, F300, PCB, BPL, CAL, CPG, and APC" manufactured by Toyo Carbon Co., Ltd.; "Kuraray Coal KW" manufactured by KURARAY CHEMICAL CO., LTD.; "BAC" manufactured by KUREHA CHEMICAL INDUSTRY CO., LTD.; and "PN, ZN, SA, SA-SW, SX, CA, CN, CG, D-10, W, GL, and HB PLUS" manufactured by Norit Japan Co., Ltd. When using the fibrous activated carbon, it is possible to use "FX-300" manufactured by Toyo Rayon Co., Ltd.; "M-30" manufactured by Osaka Gas Co., Ltd.; and "KF-1500" manufactured by TOYOBO CO., LTD. When using the sheet-like activated carbon, it is possible to use "Microlite AC" manufactured by Kanebo, Ltd.

The amount of the activated carbon used in the production method of the present invention is not specifically limited as long as the intramolecular dehydration reaction of the raw material carbohydrate progresses, and can be adjusted in a range of 0.01 to 1.0 part by mass, and preferably 0.03 to 0.3 parts by mass or 0.01 to 0.1 parts by mass, based on 1 part by mass of a carbohydrate per solid content.

A part of the produced 5-HMF is sometimes adsorbed on the activated carbon in the production method of the present invention. However, the 5-HMF adsorbed on the activated carbon can also be recovered by washing the activated carbon with water, an organic solvent or the like in order to improve the yield.

The activated carbon is preferred because of its low cost as compared with conventional liquid acid catalysts and solid acid catalysts and additionally its less risk in view of sanitation and high safety in handling, or even when it remains in the product. The activated carbon can be easily separated from the reaction system by sedimentation, filtration, centrifugation, or use in the form of a packed column.

The activated carbon is also preferred in view of economy since it is excellent in reusability and can be repeatedly used. The method of reusing the activated carbon of the present invention can be an existing method and is not specifically limited. For example, it is possible to use a vacuum regeneration method in which an adsorbate is desorbed by decreasing the solute concentration of a solvent and pressure; a solvent regeneration method involving extraction with a solvent; a substitution regeneration method involving substitution with any other adsorbate; a heat desorption method by heating; a chemical regeneration method by chemical treatment; and an oxidative decomposition regeneration method by oxidation and decomposition.

In the production method of the present invention, the reaction of the present invention may be carried out by using, in addition to the activated carbon, a catalyst other than the activated carbon. Examples of the catalyst, which can be used together with the activated carbon, include acid catalysts, and specific examples of the acid catalysts include liquid acid catalysts such as hydrochloric acid and phosphoric acid and solid acid catalysts such as ion exchange resins. Nonvolatile catalysts are preferred from the viewpoint that such catalysts can be easily removed from the reaction system, and nonvolatile solid catalysts are more preferred.

The method for producing 5-HMF of the present invention is characterized by using, as a raw material, a carbohydrate comprising a hexose as a constituent sugar or a derivative thereof. The carbohydrate used as a raw material may be a hexose itself (monosaccharide) or a sugar polymer (oligosaccharide or polysaccharide) comprising a hexose as a constituent sugar. Examples of the hexose include fructose, glucose, galactose, mannose, psicose, sorbose, and tagatose. In consideration of the economy, easiness of acquisition and the like, fructose and glucose are preferred, and fructose is especially preferred. The sugar polymer comprising a hexose as a constituent sugar is not particularly limited. Examples of the sugar polymer include mannobiose, lactose, lactulose, mannan, galactan, arabinogalactan, and xyloglucan. In consideration of the economy, a sugar polymer comprising a hexose as a constituent sugar is preferably used. In consideration of the economy, easiness of acquisition and the like, a sugar polymer comprising fructose and/or glucose as a constituent sugar is more preferred, and examples thereof include sucrose, maltose, trehalose, turanose, isomaltulose, cellobiose, isomaltose, nigerose, maltulose, isomaltulose, gentiobiose, maltotriose, 1-kestose, maltooligosaccharide, fructooligosaccharide, dextrin, dextran, inulin, levan, starch, and cellulose. Sucrose, inulin and starch are particularly preferred. When a sugar polymer comprising a hexose as a constituent sugar is used as a raw material carbohydrate, it is possible to further convert the carbohydrate into 5-HMF through an intramolecular dehydration reaction using an activated carbon catalyst simultaneously or sequentially while supplying the hexose through decomposition of the carbohydrate at the time of a heating reaction.

The derivative of the carbohydrate is not particularly limited as long as it has a functional group such as a hydroxyl group to be subjected to the dehydration reaction, and examples thereof include modified sugars such as amino sugar, etherified sugar, halogenated sugar and phosphorylated sugar. Examples of such derivatives include glucosamine, glucose-6-phosphoric acid, and methyl α-D-mannopyranoside.

As the raw material carbohydrate of the present invention, fructose and/or glucose are preferably used in view of their reactivity, easiness of obtainment, price, and the like, and fructose is more preferably used. The raw material carbohydrate to be used in the present invention may be a pure product, but can also be a carbohydrate composition which is a mixture of a plurality of carbohydrates. When the carbohydrate composition is used as a raw material carbohydrate for the production method of the present invention, the carbohydrate composition preferably contains fructose in an amount of 10% by mass or more per solid content, more preferably contains fructose in an amount of 30% by mass or more per solid content.

The nature of the carbohydrate which serves as the raw material for the production method of the present invention is not particularly limited as long as the reaction progresses. The carbohydrate may be in the form of a crystal, non-crystalline powder or solution, but is preferably in the form of a solution from the viewpoint of reaction efficiency and economy. The solid content concentration of the solution is also not particularly limited. The solid content concentration of the solution is preferably 1% by mass to 85% by mass, more preferably 5% by mass to 80% by mass, particularly preferably 20% by mass to 75% by mass. The use of a solution having a solid content concentration not higher than a certain level can further suppress the production of a sugar condensate as a byproduct, and the use of a solution having a solid content concentration not lower than a certain level can efficiently promote the reaction. The solvent constituting the reaction solution is also not particularly limited, and examples thereof include water; organic solvents such as ethanol, methanol, isopropanol, acetone, acetonitrile, methyl isobutyl ketone, and dimethyl sulfoxide; and ion liquids such as 1-butyl-3-methylimidazolium tetrafluoroborate and 1-butyl-3-methylimidazolium hexafluorophosphate. These solvents may be used singly or mixed in any ratio for use. In consideration of the reaction efficiency and the like, an organic solvent is preferably used as the solvent. In consideration of the cost, safety and the like, water (aqueous solution) is preferably used as the solvent. Also, in consideration of the price, easiness of obtainment and the like, an isomerized syrup (fructose glucose syrup, glucose fructose syrup, or high-fructose syrup) is particularly suitable as the raw material for the production method of the present invention.

Any reaction conditions may be employed in the production method of the present invention as long as 5-HMF is produced through an intramolecular dehydration reaction. From the viewpoint of efficient production of 5-HMF from fructose, for example, the reaction temperature (product temperature of the raw material carbohydrate) can be set to 100 to 400° C. (preferably 110 to 250° C., more preferably 110 to 200° C., particularly preferably 120 to 180° C., most preferably 130 to 170° C.), and the reaction time can be set to 0.2 to 10 hours (preferably 0.5 to 6 hours, more preferably 1 to 4 hours).

The reaction temperature and reaction time can be appropriately adjusted. For example, the reaction time can be shortened since the concentration of 5-HMF can be increased quickly by increasing the reaction temperature. On the other hand, the reaction temperature can be decreased since the concentration of 5-HMF can be increased by prolonging the reaction time. However, byproducts due to overreactions are easily produced at excessively high temperatures, and thus it is possible to decrease the substrate concentration to conduct a reaction. Also, at low temperatures, it is possible to increase the substrate concentration to conduct a reaction.

The reaction conditions are appropriately set as described above, so that the production method of the present invention can serve as a method for producing a carbohydrate composition comprising, for example, 5% by mass of 5-HMF per solid content of the composition. In the production method of the present invention, a method for producing a carbohydrate composition comprising preferably 7% by mass or more of 5-HMF per solid content of the composition, more preferably 10% by mass or more of 5-HMF per solid content of the composition can be used.

The pressure at the reaction is also not particularly limited in the production method of the present invention, and the reaction may be performed under any of normal pressure conditions, pressurization conditions and reduced pressure conditions, but, from the viewpoint of the reaction efficiency, is performed preferably under pressurization conditions, more preferably under the pressure conditions of 1 to 9 kgf/cm$^2$. The reaction is performed under the pressurization conditions, thereby making it possible to further reduce the production of a byproduct sugar condensate.

In the production method of the present invention, the 5-HMF obtained by the dehydration reaction or a composition comprising the 5-HMF can be used as it is for that purpose. According to need, the reaction product may be, for example, centrifuged or filtered to remove insoluble matter and then subjected to resin fractionation or extraction treatment with a solvent.

As will be described in the Examples below, a carbohydrate composition comprising 5-HMF can be produced by subjecting a carbohydrate composition comprising a carbohydrate comprising at least a hexose as a constituent sugar to heating treatment in the presence of activated carbon. Thus, according to another aspect of the present invention, there is provided a method for producing a carbohydrate composition comprising 5-HMF by heating a carbohydrate composition comprising one or more selected from the group consisting of carbohydrates comprising a hexose as a constituent sugar and derivatives thereof, in the presence of activated carbon, at a temperature of 100° C. to 400° C. This production method can be carried out according to the descriptions about the method for producing 5-HMF according to the present invention.

The production method of the present invention makes it possible to inexpensively and simply produce 5-HMF on an industrial scale, as described above. The production method of the present invention also has the features of reduction in production of byproducts that can be produced through a heating reaction to improve the yield, possible continuous use of producing facilities, and further a low degree of coloration of the reaction product. Briefly, the production method of the present invention is advantageous in that 5-HMF with a high commercial value can be produced on an industrial scale.

The 5-HMF obtained by the production method of the present invention can be utilized as a raw material for resins such as biomass plastics. Examples of the resin made from 5-HMF as a raw material or an intermediate for its production include polyethylene furanoate and 2,5-furandicarboxylic acid.

Namely, the present invention provides a method for producing 2,5-furandicarboxylic acid or an ester thereof, comprising subjecting the 5-HMF obtained by the production method of the present invention to an oxidation reaction to obtain 2,5-furandicarboxylic acid, and optionally esterifying the 2,5-furandicarboxylic acid. The method comprising subjecting 5-HMF to an oxidation reaction to produce 2,5-furandicarboxylic acid is known to those skilled in the art, and can be carried out with reference to the descriptions of WO 2008/054804, JP 2015-83559 A, JP 2008-88134 A and the like. As an example, 2,5-furandicarboxylic acid can be produced by oxidizing 5-HMF in the presence of a metal catalyst (for example, platinum, palladium, bismuth, tin, rhenium, copper, silver, magnesium or manganese). This oxidation reaction can be carried out, for example, at a temperature of 30° C. to 180° C. and a pressure of 1.0 kgf/cm$^2$ to 16.3 kgf/cm$^2$. Also, the esterification of 2,5-furandicarboxylic acid can be performed according to a normal method. Examples of esters of 2,5-furandicarboxylic acid include esters thereof with a volatile alcohol or phenol, and methyl esters and ethyl esters are preferred.

Also, the present invention provides a method for producing a copolymer, comprising the steps of subjecting, to an oxidation reaction, the 5-HMF obtained by the production method of the present invention to obtain 2,5-furandicarboxylic acid or an ester thereof, and copolymerizing the 2,5-furandicarboxylic acid or ester thereof with a different copolymerizable monomer. The copolymerizing step can be carried out by conducting a transesterification reaction or esterification reaction to obtain a prepolymer (lower polymer), and then subjecting the prepolymer to a polycondensation reaction to obtain a high-molecular-weight copolymer. The copolymerizing step can also be carried out by subjecting a copolymerizable monomer comprising 2,5-furandicarboxylic acid or an ester thereof to a polycondensation reaction to obtain a high-molecular-weight copolymer. Here, the transesterification reaction refers to the step of transesterifying the carboxylic acid ester which constitutes the copolymer of the present invention with an alcohol component at a predetermined temperature to obtain a prepolymer. The esterification reaction refers to the step of esterifying the carboxylic acid component which constitutes the copolymer of the present invention with an alcohol component at a predetermined temperature to obtain a prepolymer. The polycondensation reaction refers to the step of subjecting the prepolymer obtained by the transesterification or esterification reaction or a copolymerizable monomer to pressure reduction treatment to initiate a polymerization reaction, thereby obtaining a high-molecular-weight copolymer.

Examples of the different copolymerizable monomer that can be used in the production method of the present invention include compounds having two or more hydroxyl groups. The copolymerizable monomer is preferably a diol compound or polyol compound, more preferably ethylene glycol and 1,4-butanediol. When ethylene glycol is used as the different copolymerizable monomer in the production method of the present invention, the final product copolymer (resin composition) is polyethylene furanoate. In the production method of the present invention, a diol such as diethylene glycol, propylene glycol, 1,3-propanediol, 1,4-butanediol, 1,5-pentanediol, cyclobutanedimethanol, cyclohexanedimethanol, 2,5-furandimethanol or isosorbide can be used as the different copolymerizable monomer to obtain a copolymer. A method comprising subjecting 2,5-furandicarboxylic acid or an ester thereof to a copolymerization reaction (polycondensation reaction) with a copolymerizable monomer (especially, ethylene glycol), thereby producing a copolymer (especially, polyethylene furanoate) is known to those skilled in the art. For example, the method can be carried out with reference to the descriptions of WO 2010/077133, JP 2015-506389 T and the like. As an example, polyethylene furanoate (PEF) can be produced by subjecting an ester of 2,5-furandicarboxylic acid and ethylene glycol to a transesterification reaction using titanium (IV) isopropoxide ($Ti[OCH(CH_3)_2]_4$) as a catalyst, and then polycondensing the transesterification product under a reduced pressure. The transesterification reaction can be carried out at 150° C. to 220° C., and the polycondensation reaction can be carried out within a temperature range between the melting point of the copolymer and a temperature 30° C. higher than the melting point (but about 180° C. or higher) under a high vacuum.

The 5-HMF or derivative thereof obtained by the production method of the present invention can be utilized, for example, as a fragrance imparting component, a physiologically active component, a food raw material, and a pharmaceutical raw material (for example, JP 2015-211669 A, JP 2008-193933 A, JP 2006-508998 T, JP 2010-248107 A and JP 2011-136959 A). The activated carbon used as the catalyst has been confirmed to be safe to humans, as can be understood from the fact that it has been utilized as a food additive. Therefore, the produced 5-HMF or derivative thereof is advantageous in that it can be applied as it is as a food or pharmaceutical raw material. Namely, the present invention provides a method for producing a pharmaceutical or food product, comprising carrying out the production method of the present invention to produce 5-HMF, optionally derivatizing the obtained 5-HMF, and blending the obtained 5-HMF or derivative thereof to a pharmaceutical or food raw material. The method for producing a pharmaceutical or food product can be carried out according to normal procedures for producing a pharmaceutical or food product except the step of blending the 5-HMF or derivative thereof, of course. Examples of the derivative of 5-HMF include 5-methoxymethyl-2-furfural, and the derivative can be produced, for example, according to the descriptions of JP 2010-538033 T.

The 5-HMF or derivative thereof obtained by the production method of the present invention can also be used as a raw material for synthesis of a pharmaceutical product. For example, 5-HMF is admitted as a sovereign medicine for sickle cell disease by the United States Food and Drug Administration (FDA).

The present invention provides a catalyst composition for use in the reaction for producing 5-HMF, through a dehydration reaction, from a carbohydrate comprising a hexose as a constituent sugar, the catalyst composition comprising activated carbon as an active ingredient. The catalyst composition can be used in a method for producing 5-HMF by subjecting a carbohydrate raw material comprising a hexose as a constituent sugar, such as fructose, to a dehydration reaction, like the above production method. The catalyst composition may appropriately comprise other components (a liquid acid catalyst such as hydrochloric acid or phosphoric acid, a solid acid catalyst such as an ion exchange resin, etc.) in addition to activated carbon. The catalyst composition of the present invention can be carried out according to the descriptions about the production method of the present invention.

Also, the present invention provides use of activated carbon and a composition comprising the activated carbon, as a catalyst for a reaction for producing 5-hydroxymethyl-2-furfural from a carbohydrate comprising a hexose as a constituent sugar or a derivative thereof through a dehydration reaction. Further, the present invention provides use of activated carbon and a composition comprising the activated carbon, for the manufacture of a catalyst for a reaction for producing 5-hydroxymethyl-2-furfural from a carbohydrate comprising a hexose as a constituent sugar or a derivative thereof through a dehydration reaction. The uses according to the present invention can be carried out according to the descriptions about the production method of the present invention and the catalyst composition of the present invention.

EXAMPLES

Hereinafter, the present invention will be described in more detail by way of the following examples, but is not limited thereto. Unless otherwise noted herein, the unit "%" represents % by mass, and, when reference is made to the proportion (content) per "solid content" or the content proportion (concentration) of the "solid content," it means a proportion defined based on the mass of the solid component.

Example 1: Production of 5-HMF Using Various Catalysts and Analysis (1) Preparation of Samples A high fructose syrup (fructose content per solid content: 95%; solid content concentration: 75.5; product name: L-95; manufactured by Nihon Shokuhin Kako Co., Ltd.) was used as a substrate carbohydrate. The substrate carbohydrate (1.4 g (carbohydrate mass)) was put in respective reaction vessels (made of stainless steel), and various catalysts were added so as to attain the amounts (ratio % with respect to the solid content of the substrate carbohydrate) indicated in Table 1. In the following Examples, the amount (%) of the catalyst to be added means the mass of the catalyst when the mass of the solid content of the carbohydrate serving as the substrate is defined as 100%. After stirring of the respective samples, the temperature of the samples was allowed to reach 130° C. in an autoclave (manufactured by Tomy Seiko Co., Ltd., BS-325), kept at a pressure of 1.7 kgf/cm² for 3 hours, and naturally dropped to conduct a heating reaction, thereby obtaining reaction products (Reaction Products 1 to 10). After completion of the reaction, water was added to the reaction products, and the solutions were stirred and filtered through a 0.45-μm filter (manufactured by Merck Millipore Ltd.) and a 0.22-μm filter (manufactured by Merck Millipore Ltd.). The respective samples obtained by diluting the respective filtrates with water so as to attain a solid content concentration of 1.0% were used as samples for HPLC analysis and samples for analysis of the degree of coloration.

(2) Analysis of 5-HMF, Fructose and Sugar Condensate by HPLC

The conditions for HPLC used in the analysis were as follows.

<HPLC Fractionation Conditions>

Column: KS-801 (8.0 mm×300 mm) (manufactured by Showa Denko K.K.)

Flow rate: 1.0 mL/min. (constant flow rate)

Detector: RI and UV (280 nm)
Column temperature: 80° C.
Amount of sample to be injected: 10 μL On the premise that the peak appearing between at 7.5 minutes and at 8.5 minutes of the retention time in the HPLC analysis corresponded to fructose and that the peak appearing between at 16.5 minutes and at 18.5 minutes of the retention time corresponded to 5-HMF, the proportions (%) of fructose and 5-HMF to the total reaction product were calculated based on the integrated value of an RI analysis value.

Also on the premise that the peak appearing between at 0 minute and at 6 minutes of the retention time in the HPLC analysis corresponded to the sugar condensate, the content of the sugar condensate was calculated based on the integrated value of a UV analysis value.

(3) Measurement of Degree of Coloration

The absorbance at 420 nm in the solution with a solid content concentration of 1.0% prepared in the above (1) was measured with a spectrophotometer (Model U-2900, manufactured by Hitachi High-Tech Science Corporation).

(4) Evaluation of Reaction Vessel after Reaction

To measure the degree of production of byproducts in the respective reaction products, the byproducts attached to the respective reaction vessels used in the heating reaction in the above (1) were evaluated based on the following criteria.
A: Completely removed only by washing with water
B: Washed with water and then rubbed off, but somewhat remaining
C: Washed with water and then rubbed off, but not removed at all
-: Excluded from evaluation because 5-HMF was hardly produced due to insufficient reaction (5) Evaluation Results The results were as indicated in Table 1.

From the results presented in Table 1, it was revealed that, by using activated carbon as the catalyst for the dehydration reaction from fructose to 5-HMF, 5-HMF could be produced in a yield comparable to those attained by using the other catalysts. Further, it was confirmed that the use of activated carbon as the catalyst for the dehydration reaction reduced the production of the byproduct sugar condensate, significantly reduced the production of a burnt deposit-like product attached to the bottom surfaces of the reaction vessels after the reaction, and further significantly reduced the coloration of the reaction products. From the above, it was revealed that 5-HMF with a high commercial value could be produced inexpensively and simply on an industrial scale by using activated carbon as the catalyst for the dehydration reaction from fructose to 5-HMF.

Example 2: Production of 5-HMF in the Presence of Organic Solvent and Analysis (1) Preparation of Sample Fructose (manufactured by Nacalai Tesque, Inc.) was used a substrate carbohydrate. The substrate carbohydrate (0.24 g) was put in a reaction container (made of glass), and 72 mg of an activated carbon catalyst (activated carbon 2 (zinc chloride activated carbon) used in Example 1) was added thereto. Isopropanol (0.8 mL) was added, and the sample was stirred. Thereafter, the temperature of the sample was allowed to reach 150° C. in an autoclave (manufactured by Tokyo Rikakikai Co., Ltd., RCH-1000, HIP-7518), kept at a pressure of 4.9 kgf/cm$^2$ for 30 minutes, and naturally dropped to conduct a heating reaction, thereby obtaining a reaction product (Reaction Product 21). After completion of the reaction, the solution was filtered through a 0.45-μm filter (manufactured by Merck Millipore Ltd.) and a 0.22-μm filter (manufactured by Merck Millipore Ltd.).

TABLE 1

Analysis results of reaction products obtained in the presence of various catalyst

| Reaction product | Catalyst | Amount (%) of catalyst added | Composition (%) *RI analysis value Fructose | Composition (%) *RI analysis value 5-HMF | Sugar condensate content (area) *UV analysis value | State of reaction vessel | Coloration (420 nm) |
|---|---|---|---|---|---|---|---|
| 1 | None | — | 62.4 | 5.8 | 2111310 | A | 0.359 |
| 2 | Phosphoric acid | 3 | 30.7 | 37.6 | 17857551 | C | 1.663 |
| 3 | Hydrochloric acid | 3 | 6.2 | 14.8 | 22568538 | C | 1.762 |
| 4 | Activated carbon 1 (steam activated carbon) | 30 | 65.8 | 9.4 | 553153 | A | 0.017 |
| 5 | Activated carbon 2 (zinc chloride activated carbon) | 30 | 43.8 | 30.9 | 2897551 | A | 0.090 |
| 6 | Activated carbon 3 (phosphoric acid activated carbon) | 30 | 50.2 | 27.0 | 2583412 | A | 0.045 |
| 7 | Activated carbon 4 (phosphoric acid activated carbon) | 30 | 51.8 | 26.1 | 3698559 | A | 0.035 |
| 8 | Titanium oxide | 30 | 59.9 | 12.4 | 12669461 | B | 1.070 |
| 9 | Diatomaceous earth | 30 | 79.4 | 3.3 | 10179255 | — | 1.014 |
| 10 | Ion exchange rein | 30 | 29.6 | 22.2 | 23477902 | C | 2.098 |

After evaporation of isopropanol, the resultant matter was dissolved in water, and the solution was filtered through a 0.22-μm filter (manufactured by Merck Millipore Ltd.). The resultant sample was used as a sample for HPLC analysis.

(2) Analysis of 5-HMF and Fructose by HPLC

The conditions for HPLC used in the analysis were as follows.

<HPLC Fractionation Conditions>

Column: KS-801 (8.0 mm×300 mm) (manufactured by Showa Denko K.K.)
Flow rate: 1.0 mL/min. (constant flow rate)
Detector: RI
Column temperature: 80° C.
Amount of sample to be injected: 99 μL On the premise that the peak appearing between at 7.5 minutes and at 8.5 minutes of the retention time in the HPLC analysis corresponded to fructose and that the peak appearing between at 16.5 minutes and at 18.5 minutes of the retention time corresponded to 5-HMF, the proportions (%) of fructose and 5-HMF to the total reaction product were calculated based on the integrated value of an RI analysis value.

(3) Evaluation Results

The results were as indicated in Table 2.

TABLE 2

Analysis results of reaction product in the presence of organic solvent and activated carbon

| Reaction product | Catalyst | Amount (%) of catalyst added | Composition (%) *RI analysis value | |
| --- | --- | --- | --- | --- |
| | | | Fructose | 5-HMF |
| 21 | Activated carbon 2 | 30 | 7.4 | 65.0 |

From the results presented in Table 2, it was revealed that 5-HMF could be produced also when the organic solvent isopropanol was used while activated carbon was used as the catalyst for the dehydration reaction from fructose to 5-HMF.

Example 3: Production of 5-HMF from Various Raw Material and Analysis Carbohydrates (1) Preparation of Samples Glucose (manufactured by Kanto Chemical Co., Inc.), galactose (manufactured by Nacalai Tesque, Inc.), mannose (manufactured by Wako Pure Chemical Industries, Ltd.), sucrose (manufactured by Kanto Chemical Co., Inc.), lactose (manufactured by Kanto Chemical Co., Inc.), maltose (manufactured by Kanto Chemical Co., Inc.), sorbitol (manufactured by Mitsubishi Shoji Foodtech Co., Ltd.), fructooligosaccharide (manufactured by Wako Pure Chemical Industries, Ltd.), inulin (manufactured by Fuji Nihon Seito Corporation) and corn starch (manufactured by Nihon Shokuhin Kako Co., Ltd.) were used as substrate carbohydrates. The respective substrate carbohydrates (1.0 g) were put in respective reaction containers (made of glass), and 0.3 g of an activated carbon catalyst (activated carbon 2 (zinc chloride activated carbon) used in Example 1) was added. To these, 100.0 g of distilled water was added, and the respective samples were stirred. Thereafter, the temperature of the samples were allowed to reach 170° C. in an autoclave (product name: CPP-2000, manufactured by Sibata Scientific Technology, Ltd.), kept at a pressure of 7.6 kgf/cm$^2$ for 4 hours, and naturally dropped to conduct a heating reaction, thereby obtaining reaction products (Reaction Products 31 to 39). After completion of the reaction, the samples filtered through a 0.22-μm filter (manufactured by Merck Millipore Ltd.) were used as samples for HPLC analysis.

(2) Analysis of 5-HMF and Monosaccharide by HPLC

The conditions for HPLC used in the analysis were as follows.

<HPLC Fractionation Conditions>

Column: KS-801 (8.0 mm×300 mm) (manufactured by Showa Denko K.K.)
Flow rate: 1.0 mL/min. (constant flow rate)
Detector: RI
Column temperature: 80° C.
Amount of sample to be injected: 50 μL On the premise that the peak appearing within the retention time in the HPLC analysis of 7.0 minutes to 8.5 minutes corresponded to the monosaccharides and that the peak appearing between at 16.5 minutes and at 18.5 minutes of the retention time corresponded to 5-HMF, the proportions (%) of the various raw material carbohydrates and 5-HMF to the total reaction product were calculated based on the integrated value of an RI analysis value.

(3) Evaluation Results

The results were as indicated in Table 3.

TABLE 3

Analysis results of reaction products using various raw material carbohydrates

| Reaction product | Catalyst | Substrate | Composition (%) *RI analysis value | |
| --- | --- | --- | --- | --- |
| | | | Raw material carbohydrate | 5-HMF |
| 31 | Activated carbon 2 | Glucose | 79.7 | 10.7 |
| 32 | Activated carbon 2 | Galactose | 78.6 | 12.6 |
| 33 | Activated carbon 2 | Mannose | 66.2 | 18.9 |
| 34 | Activated carbon 2 | Sucrose | 49.3 | 28.5 |
| 35 | Activated carbon 2 | Lactose | 80.6 | 10.6 |
| 36 | Activated carbon 2 | Maltose | 81.6 | 10.0 |
| 37 | Activated carbon 2 | Fructooligo | 32.6 | 36.5 |
| 38 | Activated carbon 2 | Inulin | 16.3 | 40.6 |
| 39 | Activated carbon 2 | Corn starch | 82.8 | 8.3 |

From the results presented in Table 3, it was revealed that 5-HMF could be produced also when various hexoses other than fructose and various sugar polymers each comprising a hexose as a constituent sugar were used as the substrate carbohydrates for synthesizing 5-HMF using activated carbon as the catalyst.

Example 4: Production of 5-HMF in the Presence of Organic Solvent and Analysis (1) Preparation of Sample A high fructose syrup (fructose content per solid content: 95%; solid content concentration: 75.5; product name: L-95; manufactured by Nihon Shokuhin Kako Co., Ltd.) was used as a substrate carbohydrate. Dimethyl sulfoxide (44.0 g) was added to 59.4 g of the high fructose syrup. After thorough stirring, evaporation was performed at 80° C. with an evaporator to remove water (Solution A). Thereafter, 5.6 g of Solution A was put in a beaker, and well mixed with 22.4 g of dimethyl sulfoxide (Solution B). Then, 10.6 g of Solution B was put in a beaker, and 0.1053 g of activated carbon 3 was added and mixed well. Into a reaction container (made of glass), 0.6333 g of the thus-prepared sample was weighed out. The temperature of the sample was allowed to reach 150° C. in an autoclave (product name: RCH-1000, HIP-7518, manufactured by Tokyo Rikakikai Co., Ltd.), kept at normal pressure for 120 minutes, and naturally dropped to conduct a heating reaction, thereby obtaining a reaction product (Reaction Product 41). After completion of the reaction, pure water was added to obtain 7 ml of a reaction solution. The solution was filtered through a 0.45-μm filter (manufactured by Merck Millipore Ltd.) and a 0.22-μm filter (manufactured by Merck Millipore Ltd.). The filtered sample was used as a sample for HPLC analysis.

(2) Analysis of 5-HMF and Fructose by HPLC

The conditions for HPLC used in the analysis were as follows.

<HPLC Fractionation Conditions>

Column: KS-801 (8.0 mm×300 mm) (manufactured by Showa Denko K.K.)

Flow rate: 1.0 mL/min. (constant flow rate)

Detector: RI

Column temperature: 80° C.

Amount of sample to be injected: 10 μL

On the premise that the peak appearing between at 7.5 minutes and at 8.5 minutes of the retention time in the HPLC analysis corresponded to fructose and that the peak appearing between at 16.5 minutes and at 18.5 minutes of the retention time corresponded to 5-HMF, the proportions (%) of fructose and 5-HMF to the total reaction product were calculated based on the integrated value of an RI analysis value. Provided that the peak of dimethyl sulfoxide appearing between at 8.5 minutes and at 9.5 minutes was excluded, and that the proportions were calculated as percentages.

(3) Evaluation Results

The results were as indicated in Table 4.

TABLE 4

Analysis results of reaction product in the presence of dimethyl sulfoxide and activated carbon

| Reaction product | Catalyst | Amount (%) of catalyst added | Composition (%) *RI analysis value | |
|---|---|---|---|---|
| | | | Fructose | 5-HMF |
| 41 | Activated carbon 3 | 10 | 4.5 | 66.2 |

From the results presented in Table 4, it was revealed that 5-HMF could be produced also when the organic solvent dimethyl sulfoxide was used while activated carbon was used as the catalyst for the dehydration reaction from fructose to 5-HMF.

Example 5: Production of 5-HMF in the Presence of Organic Solvent and Analysis (1) Preparation of Sample A high fructose syrup (fructose content per solid content: 95%; solid content concentration: 75.5; product name: L-95; manufactured by Nihon Shokuhin Kako Co., Ltd.) was used as a substrate carbohydrate. Pure water was added to the high fructose syrup to adjust the solid content concentration to 51.2%. To 10.0 g of this solution, activated carbon 3 was added so that the amount thereof reached 1.0 g, and mixed well. This mixed solution (0.6604 g) was weighed out into a reaction container (made of glass), and 0.5 ml of methyl isobutyl ketone was added thereto. The sample was set in an autoclave (product name: RCH-1000, HIP-7518, manufactured by Tokyo Rikakikai Co., Ltd.). The pressure within the container was adjusted to 6.1 kgf/cm² with argon, and the temperature of the sample was allowed to reach 160° C., kept at a pressure of 8.6 kgf/cm² for 120 minutes, and naturally dropped to conduct a heating reaction, thereby obtaining a reaction product (Reaction Product 51). The recovered sample was transferred to a 50-ml pear-shaped flask while it was washed with pure water, and subjected to evaporation at 70° C. with an evaporator to remove methyl isobutyl ketone. Pure water was added again for dissolution, and the solution was filtered through a 0.22-μm filter (manufactured by Merck Millipore Ltd.). Pure water was added to the filtered sample to attain an amount of 9.0 ml. The sample solution was used as a sample for HPLC analysis.

(2) Analysis of 5-HMF and Fructose by HPLC

The conditions for HPLC used in the analysis were as follows.

<HPLC Fractionation Conditions>

Column: KS-801 (8.0 mm×300 mm) (manufactured by Showa Denko K.K.)

Flow rate: 1.0 mL/min. (constant flow rate)

Detector: RI

Column temperature: 80° C.

Amount of sample to be injected: 10 μL

On the premise that the peak appearing between at 7.5 minutes and at 8.5 minutes of the retention time in the HPLC analysis corresponded to fructose and that the peak appearing between at 16.5 minutes and at 18.5 minutes of the retention time corresponded to 5-HMF, the proportions (%) of fructose and 5-HMF to the total reaction product were calculated based on the integrated value of an RI analysis value.

(3) Evaluation Results

The results were as indicated in Table 5.

TABLE 5

Analysis results of reaction product in the presence of methyl isobutyl ketone and activated carbon

| Reaction product | Catalyst | Amount (%) of catalyst added | Composition (%) *RI analysis value | |
|---|---|---|---|---|
| | | | Fructose | 5-HMF |
| 51 | Activated carbon 3 | 20 | 20.7 | 55.4 |

From the results presented in Table 5, it was revealed that 5-HMF could be manufactured also when the organic solvent methyl isobutyl ketone was used while activated carbon was used as the catalyst for the dehydration reaction from fructose to 5-HMF.

Example 6: Production and Analysis of 5-HMF Using Activated Carbon (1) Preparation of Sample Fructose (manufactured by Nacalai Tesque, Inc.) was used as a substrate carbohydrate. Fructose was weighed out into a beaker, and pure water was added to adjust the solid content concentration to 51.2%. To this fructose solution, various catalysts were added so as to attain the amounts indicated in Table 6. After stirring of the respective samples, 0.5 ml of the samples were put in respective reaction containers (made of glass). The temperature of the samples was allowed to reach 140° C. in an autoclave (product name: RCH-1000, HIP-7518, manufactured by Tokyo Rikakikai Co., Ltd.), kept at a pressure of 2.3 kgf/cm² for 180 minutes, and naturally dropped to conduct a heating reaction, thereby obtaining reaction products (Reaction Products 61 to 64).

After completion of the reaction, water was added to the reaction products, and the solutions were stirred and filtered through a 0.45-μm filter (manufactured by Merck Millipore Ltd.) and a 0.22-μm filter (manufactured by Merck Millipore Ltd.). The respective samples obtained by diluting the respective filtrates with water so as to attain a solid content concentration of 2.0% were used as samples for HPLC analysis and samples for analysis of the degree of coloration.

(2) Analysis of 5-HMF and Fructose by HPLC

The conditions for HPLC used in the analysis were as follows.

<HPLC Fractionation Conditions>

Column: KS-801 (8.0 mm×300 mm) (manufactured by Showa Denko K.K.)

Flow rate: 1.0 mL/min. (constant flow rate)

Detector: RI

Column temperature: 80° C.

Amount of sample to be injected: 20 μL

On the premise that the peak appearing between at 7.5 minutes and at 8.5 minutes of the retention time in the HPLC analysis corresponded to fructose and that the peak appearing between at 16.5 minutes and at 18.5 minutes of the retention time corresponded to 5-HMF, the proportions (%) of fructose and 5-HMF to the total reaction product were calculated based on the integrated value of an RI analysis value.

(3) Measurement of Coloration

The absorbance at 420 nm in the solution with a solid content concentration of 2.0% prepared in the above (1) was measured with a spectrophotometer (Model U-2900, manufactured by Hitachi High-Tech Science Corporation).

(4) Evaluation Results

The results were as indicated in Table 6.

TABLE 6

Analysis results of reaction products in the presence of activated carbon

| Reaction product | Catalyst | Amount (%) of catalyst added | Composition (%) *RI analysis value | | Coloration (420 nm) |
|---|---|---|---|---|---|
| | | | Fructose | 5-HMF | |
| 61 | Activated carbon 2 | 0 | 68.6 | 6.9 | 0.729 |
| 62 | Activated carbon 2 | 1 | 67.1 | 7.9 | 0.237 |
| 63 | Activated carbon 2 | 5 | 58.4 | 15.5 | 0.237 |
| 64 | Activated carbon 2 | 10 | 54.3 | 20.6 | 0.247 |

From the results presented in Table 6, it was revealed that, in the case where activated carbon was used as the catalyst for the dehydration reaction from fructose to 5-HMF, 5-HMF could be produced also when the amount of the catalyst added was any of 1%, 5% and 10%. Also, it was revealed that when activated carbon was used, coloration was reduced as compared with the reaction product obtained without addition of activated carbon.

Example 7: Production and Analysis of 5-HMF Using Activated Carbon and Another Catalyst in Combination (1) Preparation of Sample A high fructose syrup (fructose content per solid content: 95%; solid content concentration: 75.5; product name: L-95; manufactured by Nihon Shokuhin Kako Co., Ltd.) was used as a substrate carbohydrate. Pure water was added to the high fructose syrup to adjust the solid content concentration to 61.4%. To 10.0 g of this solution, activated carbon 1 or activated carbon 5 (zinc chloride activated carbon) was added so that the amount thereof reached 0.3 g, and mixed well. The mixed solution (0.6585 g) having activated carbon 1 added thereto and 0.6686 g of a mixed solution having activated carbon 5 added thereto were weighed out into respective reaction containers (made of glass), and phosphoric acid was added to the respective mixed solutions so as to attain the amounts indicated in Table 7. The samples were each set in an autoclave (product name: RCH-1000, HIP-7518, manufactured by Tokyo Rikakikai Co., Ltd.). The temperature of the samples was allowed to reach 155° C., kept at a pressure of 2.9 kgf/cm$^2$ for 60 minutes, and naturally dropped to conduct a heating reaction, thereby obtaining reaction products (Reaction Products 71 and 72).

After completion of the reaction, water was added, and the solutions were stirred and filtered through a 0.45-μm filter (manufactured by Merck Millipore Ltd.) and a 0.22-μm filter (manufactured by Merck Millipore Ltd.). Pure water was added to the filtered samples to attain an amount of 7.0 ml, and the sample solutions were used as samples for HPLC analysis.

(2) Analysis of 5-HMF and Fructose by HPLC

The conditions for HPLC used in the analysis were as follows.

<HPLC Fractionation Conditions>

Column: KS-801 (8.0 mm×300 mm) (manufactured by Showa Denko K.K.)

Flow rate: 1.0 mL/min. (constant flow rate)

Detector: RI

Column temperature: 80° C.

Amount of sample to be injected: 10 μL

On the premise that the peak appearing between at 7.5 minutes and at 8.5 minutes of the retention time in the HPLC analysis corresponded to fructose and that the peak appearing between at 16.5 minutes and at 18.5 minutes of the retention time corresponded to 5-HMF, the proportions (%) of fructose and 5-HMF to the total reaction product were calculated based on the integrated value of an RI analysis value.

(3) Evaluation Results

The results were as indicated in Table 7.

TABLE 7

Analysis results of reaction products in the presence of activated carbon and phosphoric acid

| Reaction product | Catalyst | Amount (%) of catalyst added | Composition (%) *RI analysis value | |
|---|---|---|---|---|
| | | | Fructose | 5-HMF |
| 71 | Activated carbon 1 Phosphoric acid | 5.0 0.36 | 39.1 | 27.0 |

TABLE 7-continued

Analysis results of reaction products in the presence of activated carbon and phosphoric acid

| Reaction product | Catalyst | Amount (%) of catalyst added | Composition (%) *RI analysis value | |
|---|---|---|---|---|
| | | | Fructose | 5-HMF |
| 72 | Activated carbon Phosphoric acid | 5.0 1.44 | 18.9 | 37.1 |

From the results presented in Table 7, it was revealed that 5-HMF could be produced also when any other catalyst was used in combination with activated carbon as the catalyst for the dehydration reaction from fructose to 5-HMF.

The invention claimed is:

1. A method for producing a carbohydrate composition comprising 5-hydroxymethyl-2-furfural, comprising performing a dehydration reaction of a carbohydrate comprising a hexose as a constituent sugar or a derivative thereof by using unmodified activated carbon as a catalyst at a temperature of 110° C. to 200° C. and under a pressure of 1 to 9 kgf/cm$^2$ to thereby produce said carbohydrate composition comprising said 5-hydroxymethyl-2-furfural.

2. A method for producing a carbohydrate composition comprising 5-hydroxymethyl-2-furfural, comprising heating a carbohydrate composition comprising one or more selected from the group consisting of carbohydrates comprising a hexose as a constituent sugar and derivatives thereof in the presence of unmodified activated carbon at a temperature of 110° C. to 200° C. and under a pressure of 1 to 9 kgf/cm$^2$ to thereby produce said carbohydrate composition comprising 5-hydroxymethyl-2-furfural through an intramolecular dehydration reaction.

3. The method of claim 1, further comprising producing 2,5-furandicarboxylic acid or an ester thereof by subjecting said 5-hydroxymethyl-2-furfural to an oxidation reaction to thereby produce said 2,5-furandicarboxylic acid or an ester thereof.

4. The method of claim 3, further comprising producing a copolymer by copolymerizing the 2,5-furandicarboxylic acid or ester thereof with a different copolymerizable monomer.

5. The method according to claim 4, wherein the different copolymerizable monomer is ethylene glycol and the produced copolymer is polyethylene furanoate.

6. The method of claim 1, further comprising producing a pharmaceutical or food product by optionally derivatizing the 5-hydroxymethyl-2-furfural and blending the 5-hydroxymethyl-2-furfural or derivative thereof.

7. The method of claim 2, further comprising producing 2,5-furandicarboxylic acid or an ester thereof by subjecting said 5-hydroxymethyl-2-furfural to an oxidation reaction to thereby produce said 2,5-furandicarboxylic acid or an ester thereof.

8. The method of claim 7, further comprising producing a copolymer by copolymerizing the 2,5-furandicarboxylic acid or ester thereof with a different copolymerizable monomer.

9. The method of claim 8, wherein the different copolymerizable monomer is ethylene glycol and the produced copolymer is polyethylene furanoate.

10. The method of claim 2, further comprising producing a pharmaceutical or food product by optionally derivatizing the 5-hydroxymethyl-2-furfural and blending the 5-hydroxymethyl-2-furfural or derivative thereof.

11. The method of claim 1, wherein the carbohydrate composition comprises 7% or greater by mass of 5-hydroxymethyl-2-furfural per solid content of the composition.

12. The method of claim 2, wherein the produced carbohydrate composition comprises 7% or greater by mass of 5-hydroxymethyl-2-furfural per solid content of the composition.

13. The method of claim 1, wherein the hexose is selected from the group consisting of glucose, fructose, galactose, mannose, sucrose, lactose, maltose, fructooligosaccharide, inulin, corn starch, and mixtures thereof.

14. The method of claim 2, wherein the hexose is selected from the group consisting of glucose, fructose, galactose, mannose, sucrose, lactose, maltose, fructooligosaccharide, inulin, corn starch, and mixtures thereof.

* * * * *